United States Patent [19]
Bock et al.

[11] Patent Number: 4,594,191
[45] Date of Patent: Jun. 10, 1986

[54] PROCESS FOR PREPARING A BENZODIAZEPINEDIONE DERIVATIVE

[75] Inventors: Mark G. Bock, Hatfield; Ben E. Evans, Lansdale; Roger M. Freidinger, Hatfield; Steven M. Pitzenberger, Lansdale, all of Pa.

[73] Assignee: Merck & Co., Inc., Rahway, N.J.

[21] Appl. No.: 725,885

[22] Filed: Apr. 22, 1985

[51] Int. Cl.$^4$ .................. C07D 403/14; C07D 403/06
[52] U.S. Cl. ...................... 260/239.3 P; 260/239.3 D
[58] Field of Search .................. 260/239.3 D, 239.3 P

[56] References Cited

U.S. PATENT DOCUMENTS 4,530,790  7/1985  Monaghan et al. .......... 260/239.3 P

FOREIGN PATENT DOCUMENTS 0116150  12/1985  European Pat. Off. ...... 260/239.3 P

OTHER PUBLICATIONS

M. Gates, J. Org. Chem., (1980) 45 1675.
R. Gompper & W. Breitschaft Angeu, Chem. Int. Ed., (1983) 22 717.

*Primary Examiner*—Robert T. Bond
*Attorney, Agent, or Firm*—Daniel T. Szura; Hesna J. Pfeiffer; Julian S. Levitt

[57] ABSTRACT

A non-fermentation process for preparing a benzodiazepinedione of the formula:

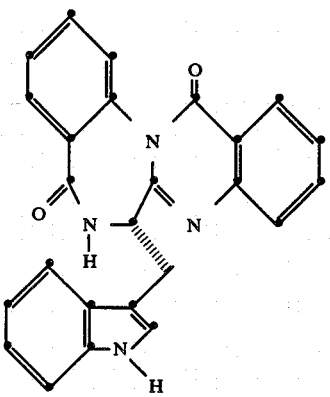

and intermediates is disclosed.

5 Claims, No Drawings

PROCESS FOR PREPARING A BENZODIAZEPINEDIONE DERIVATIVE

BACKGROUND OF THE INVENTION

This invention relates to a non-fermentation route to a benzodiazepinedione having cholecystokinin (CCK) inhibiting activity.

The compound:

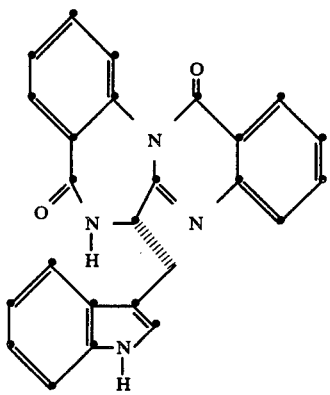

X is disclosed in published European application No. 116,150. This compound is active as a CCK inhibitor. The compound is shown to be prepared by fermentation.

A non-fermentation process for preparation of X has been discovered.

SUMMARY OF THE INVENTION

A process for non fermentation synthesis of the X compound and intermediates.

DETAILED DESCRIPTION OF THE INVENTION

An embodiment of the invention is a process for preparing a compound of the formula:

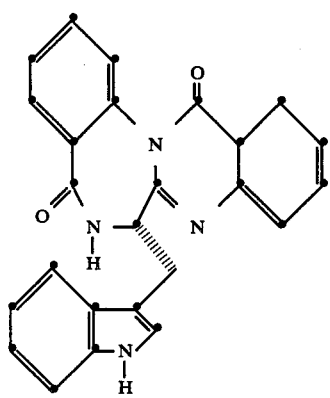

X which comprises (a) treating tryptophan with isatoic anhydride to obtain a compound of the formula:

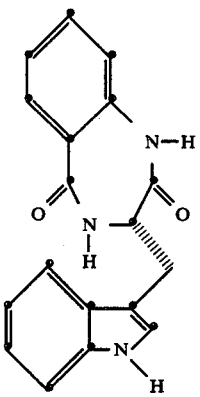

A (b) treating A with Lawesson's Reagent to obtain a compound of the formula:

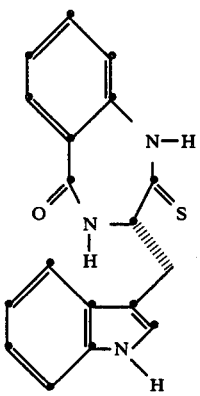

B (c) treating B with RI wherein R is lower alkyl (having 1-6 and preferably 1-3 carbon atoms) to obtain a compound of the formula:

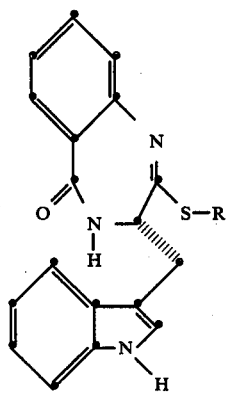

C and (d) condensing C with

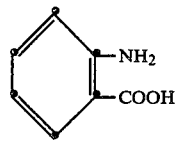

to obtain X.

The following set of equations concisely illustrates the present process:

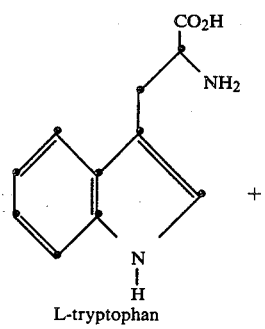
L-tryptophan

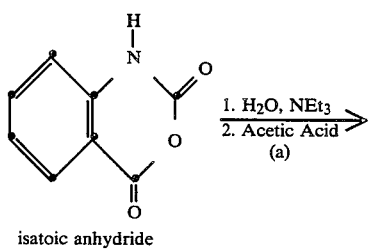
isatoic anhydride

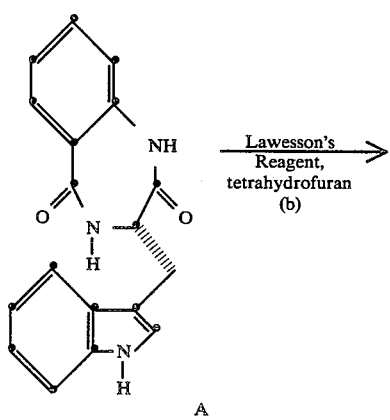
A

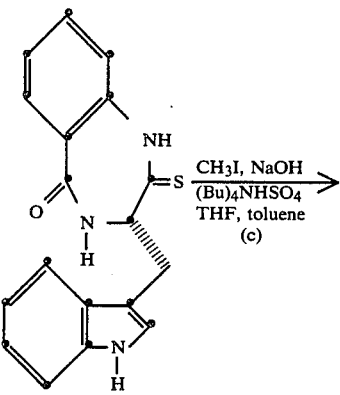
B

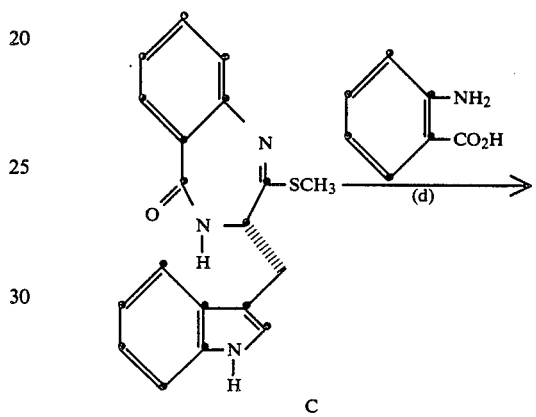
C

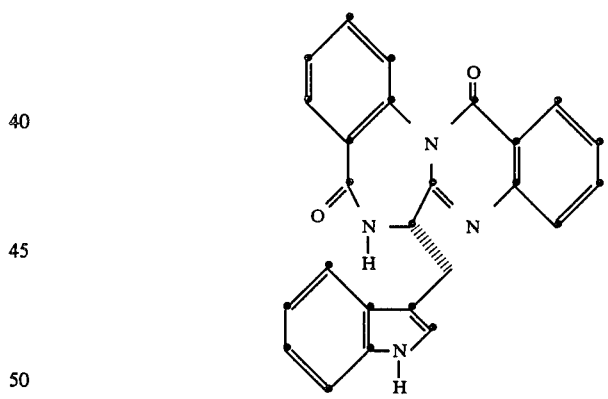
X

Step (a)

The reaction of tryptophan with isatoic anhydride is generally carried out by suspending the reactants in an aqueous medium containing an amine base such as triethylamine and the like and stirring the mixture at room temperature for a period of time (16 hours). The water is removed, e.g. by vacuum, and an organic acid e.g. acetic acid is added. The mixture is refluxed for a period of time (4 to 5 hours). The product A is recovered in a conventional manner (cf M. Gates, *J. Org. Chem.*, (1980) 45, 1675).

Step (b)

The A compound is treated with 2,4-bis(4-methoxyphenyl)-2,4-dithioxo-1,3,2,4-dithiaphosphetane (Lawesson's reagent) in a suitable reaction medium e.g. tetrahydrofuran (THF). This reaction is generally carried out at room temperature while protecting the mixture from moisture. The product B is then conventionally isolated from the reaction mixture.

Step (c)

The B compound is treated with an $C_1$–$C_4$ alkyliodide e.g. $CH_3I$ in a suitable solvent system such as water/toluene/THF containing a phase transfer catalyst such as tetra-n-butyl ammonium hydrogen sulfate and a base such as sodium or potassium hydroxide. The product C is conventionally recovered from this reaction mixture.

Step (d)

The C compound is condensed with anthranilic acid generally at elevated temperature (170° C. to about 180° C.). The X product is recovered conventionally from the reaction mixture.

The following example illustrates the process of the present invention. Temperatures are in °C. unless otherwise noted.

EXAMPLE 1

Step A 3,4-Dihydro-3(L)-(1H-indol-3-ylmethyl) 1H-1,4-benzodiazepine-2,5-dione, A L-Tryptophan (4.08 g, 20 mmole) and isatoic anhydride (3.26 g, 20 mmole) were suspended in a solution of triethylamine (2.8 ml, 20 mmole) in water (20 ml) and stirred at room temperature for 16 hours. The solvent was removed in vacuo (water aspirator, 80° C. bath). Acetic acid (60 ml) was added and the reaction was heated to reflux for 4 hours. Solvent was removed under reduced pressure (water aspirator, 80° C. bath) and the residue was dissolved in methanol (75 ml). Diethyl ether was added until the solution turned cloudy (125 ml). Crystallization ensued during several days of stirring at room temperature. The crude product was collected and washed with diethyl ether giving a tan solid (3.46 g). Chromatography (silica gel; 5% MeOH in $CH_2Cl_2$) afforded the benzodiazepine A as a light tan solvate. Pure product A was obtained by drying in vacuum (0.01 mm, 150° C.). m.p. 247°–8.5° C.

Step B 1,2,3,4-Tetrahydro-3(L)-(1H-indol-3-ylmethyl)-2-thioxo-5H-1,4-benzodiazepine-5-one, B To a suspension of 5.93 g (19.42 mmole) of 3,4-dihydro-3(L)-(1H-indol-3-ylmethyl)-1H-1,4-benzodiazepine-2,5-dione in 75 ml of dry tetrahydrofuran was added 4.71 g (11.65 mmole) of 2,4-bis-(4-methoxyphenyl)-2,4-dithioxo-1,3,2,4-dithiadiphosphetane (Lawesson's reagent). The reaction mixture was protected from moisture and stirred at room temperature for 2 hours. The resulting clear solution was then partitioned between ethyl acetate and water. The organic phase was washed with 10% sodium hydroxide solution and brine, then dried ($MgSO_4$) and concentrated. The residual semi-solid was purified by flash chromatography on silica gel (hexane-ethyl acetate elution 1:2 v/v) to afford 2.04 g of the desired product B. m.p. 236°–237° C.; MS (20 ev), 321 ($M^+$), 192, 130; IR (KBr, partial) 3340, 1660, 1395, 1155, 760 $cm^{-1}$; 'HNMR ($CD_3OD$) δ 3.25 (1H, brs), 3.50 (1H, brs), 4.35 (1H, brs), 6.94 (1H, t, J=8), 7.05 (1H, t, J=8), 7.11 (1H, brs), 7.22 (1H, d, J=8), 7.30 (1H, d, J=8), 7.32 (1H, t, J=8), 7.38 (1H, d, J=8), 7.57 (1H, t, J=8), 7.79 (1H, brs), 7.81 (1H, brs).

Elem. Analysis Calc. for $C_{18}H_{15}N_3OS$: N, 13.07; C, 67.27; H, 4.70. Found: N, 13.39; C, 67.39; H. 4.62.

Step C 1,3-Dihydro-3(L)-(1H-indol-3-ylmethyl)-2-(methylthio)-5H-1,4-benzodiazepine-5-one, C 1,2,3,4-Tetrahydro-3(L)-(1H-indol-3-ylmethyl)-2-thioxo-5H-1,4-benzodiazepine-5-one (707 mg, 2.20 mmole) was dissolved in 18 ml of toluene:THF (2:1). To this solution was added 3 ml of 20% sodium hydroxide solution and 713 mg (2.10 mmole) of tetra-n-butyl ammonium hydrogensulfate. The reaction mixture was cooled to 0° C. with stirring and was then treated with iodomethane (137 μl, 2.20 mmole). After 10 minutes, the reaction mixture was roto-evaporated and the residue partitioned between ethyl acetate (100 ml) and water (50 ml). The organic phase was washed with water and brine, dried ($MgSO_4$) and concentrated to afford 900 mg of a foam C. Flash chromatography on silica gel (hexane-ethyl acetate elution, 1:1 v/v) afforded the analytical sample of C: 'HNMR ($CDCl_3$) δ 2.42 (3H, s), 3.25 (2H, m), 4.0 (1H, m), 6.85 (1H, d, J 2), 7.0–7.65 (8H, m), 7.85 (1H, dxd, J=8,1), 8.35 (1H, brs).

Step D 6,7-Dihydro-7(L)-(1H-indol-3-ylmethyl)-quinazolino[3,2-a][1,4]benzodiazepine-5,13-dione, X An intimate mixture of 1,3-dihydro-3(L)(1H-indol-3-ylmethyl)-2-(methylthio)-5H-1,4-benzodiazepine-5-one (116.3 mg, 0.346 mmole) and anthranilic acid (474.4 mg, 3.46 mmole) was immersed in a preheated oil bath at 175° C. for 50 minutes. Excess anthranilic acid was sublimed from the reaction vessel under reduced pressure and the residual melt was cooled and triturated with ether. The resulting tan solid was collected and chromatographed on silica gel (chloroform-methanol-concentrated ammonia elution, 95:5:0.5 v/v) to afford 75 mg of the title compound X. Recrystallization from methylene chloride-methanol afforded white stars identical in all respects (MS, IR, 'HNMR, $^{13}CNMR$, and mp) with the authentic material (cf published European patent application No. 116150).

Claims to the invention follow.

What is claimed is:

1. A process for preparing a compound of the formula:

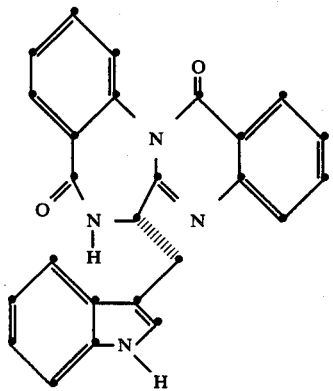

X which comprises (a) treating tryptophan with isatoic anhydride to obtain a compound of the formula:

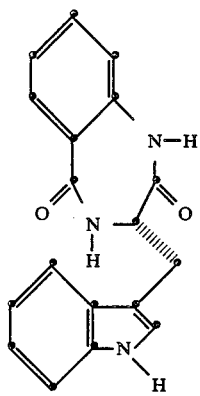

A (b) treating A with Lawesson's Reagent to obtain a compound of the formula:

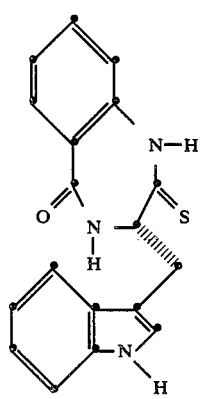

B (c) treating B with RI wherein R is lower alkyl to obtain a compound of the formula:

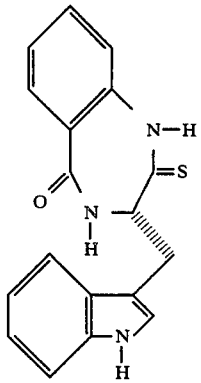

C and
(d) condensing C with

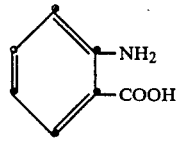

to obtain X.

2. The process of claim 1 wherein Step (a) is carried out in an aqueous basic medium followed by treatment with an acid.
3. The process of claim 1 wherein the tryptophan is L-tryptophan.
4. The process of claim 1 wherein R is CH$_3$.
5. A compound of one of the formulae:

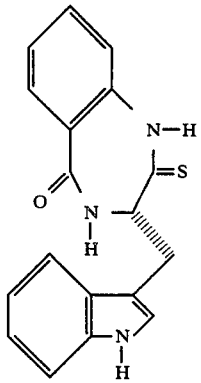

B or

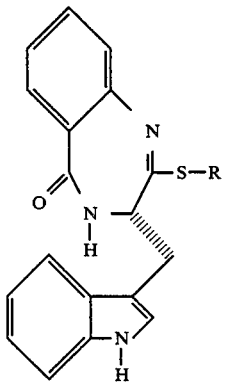

C wherein R is lower alkyl.

* * * * *